United States Patent [19]
Kroll et al.

[11] Patent Number: 5,735,878
[45] Date of Patent: *Apr. 7, 1998

[54] IMPLANTABLE DEFIBRILLATOR HAVING MULTIPLE PATHWAYS

[75] Inventors: Mark W. Kroll, Minnetonka; Theodore P. Adams, Edina; Charles G. Supino, Arden Hills, all of Minn.

[73] Assignee: Angeion Corporation, Plymouth, Minn.

[*] Notice: The term of this patent shall not extend beyond the expiration date of Pat. No. 5,306,291.

[21] Appl. No.: 577,949

[22] Filed: Dec. 22, 1995

Related U.S. Application Data

[62] Division of Ser. No. 231,036, Apr. 22, 1994, Pat. No. 5,514,160, which is a division of Ser. No. 841,544, Feb. 26, 1992, Pat. No. 5,306,291.

[51] Int. Cl.⁶ .......................................... A61N 1/36
[52] U.S. Cl. .......................................... 607/5
[58] Field of Search .......................................... 607/5, 6, 7

[56] References Cited

U.S. PATENT DOCUMENTS

| | | |
|---|---|---|
| 3,236,239 | 2/1966 | Berkorits . |
| 3,389,704 | 6/1968 | Buchowski et al. . |
| 4,168,711 | 9/1979 | Cannon, III et al. . |
| 4,499,907 | 2/1985 | Kallok et al. . |
| 4,548,203 | 10/1985 | Tacker, Jr. et al. . |
| 4,662,377 | 5/1987 | Heilman et al. . |
| 4,708,145 | 11/1987 | Tacker et al. . |
| 4,727,877 | 3/1988 | Kallok . |
| 4,800,883 | 1/1989 | Winstrom . |
| 4,811,156 | 3/1989 | Kroll . |
| 4,817,608 | 4/1989 | Shapland et al. . |
| 4,821,723 | 4/1989 | Baker, Jr. et al. . |
| 4,944,300 | 7/1990 | Sakesena . |
| 4,953,551 | 9/1990 | Mehra . |
| 4,964,406 | 10/1990 | Carroll et al. . |
| 4,969,463 | 11/1990 | Dahl et al. . |
| 4,998,531 | 3/1991 | Bochhi et al. . |
| 5,050,601 | 9/1991 | Kupersmith et al. . |
| 5,083,562 | 1/1992 | de Coriolis et al. . |
| 5,107,834 | 4/1992 | Ideker et al. . |
| 5,111,811 | 5/1992 | Smits .......................................... 607/5 |
| 5,131,388 | 7/1992 | Pless et al. . |
| 5,133,353 | 7/1992 | Hauser . |
| 5,163,427 | 11/1992 | Keimel . |
| 5,199,429 | 4/1993 | Kroll et al. . |
| 5,209,229 | 5/1993 | Gilli .......................................... 607/122 |
| 5,261,400 | 11/1993 | Bardy .......................................... 607/5 |
| 5,306,291 | 4/1994 | Kroll et al. . |
| 5,324,309 | 6/1994 | Kallok . |
| 5,376,105 | 12/1994 | Hedberg . |
| 5,385,575 | 1/1995 | Adams . |

FOREIGN PATENT DOCUMENTS

| | | |
|---|---|---|
| 0281219 | 7/1988 | European Pat. Off. . |
| 0326290 | 2/1989 | European Pat. Off. . |

OTHER PUBLICATIONS

J. N. Wetherbee, et al., "Nonthroctomy Internal Defibrillation in Dogs: Threshold Reduction Using a Subcutaneous Chest Wall Electrode with a Transvenous Catheter Electrode", J. Am. Coli. Cardiol., vol. 10, p. 406, Aug. 1987.

J. N. Wetherbee, et al., "Sequential Shocks are Comparable to Single shocke Employing Two Current Pathways for Internal Defibrillation in Dogs", PACE, vol. 11, p. 696, Jun., 1988.

Pelesica, B., Cir. Research, vol. XVIII, pp. 10–17, Jan. 1966.

(List continued on next page.)

*Primary Examiner*—Scott Getzow
*Attorney, Agent, or Firm*—Brad Pedersen

[57] ABSTRACT

An implantable defibrillator derives a rectangular current waveform from a capacitor discharge by using a current limiter. This pulse-shaping method is equally applicable to single-path and multiple-path situations. A rectangular pulse delivers a maximum of energy for a given peak-field value with a particular electrode combination and pulse duration. Peak field is a measure of the tissue-damage potentiality of a particular discharge.

10 Claims, 7 Drawing Sheets

OTHER PUBLICATIONS

Schuder, J. et al., Trans. Am. Soc. Artif. Organs vol. 15, pp. 207–212, 1970.

Echt, M.D., et al., Circulation, vol. 71, No. 2, February 1985.

JD Bourland, WA Tacker, and LA Geddes,"Strength duration curves for trapezoidal waveforms of various tilts for transchest defibrillation in animals," *Med. Instr.*, vol 12 #1, pp. 38–41, 1978.

JD Bourland, WA Tacker, LA Geddes, et al, "Comparative efficacy of damped since wave and square wave current for transchest ventricular defibrillation in animals," *Medical Instrum.*, vol. 12, #1, pp. 38–41, 1978.

LA Geddes, MJ Niebauer, CF Babbs, et al, "Fundamental criteria underlying the efficacy and safety of defibrillating current waveforms," *Med. Biol. Eng. Comp.* vol. 23, pp. 122–130, 1985.

MS Chang, H Inoue, MJ Kallok, et al, "Double and triple sequential shocks reduce ventricular defibrillation threshold in dogs with and without myocardial infarction," *J. Am. Coll. Cardiol.*, vol. 8 #6, pp. 1393–1405, Dec. 1986.

DL Jones, GJ Klein, GM Guiraudon, "Internal cardiac defibrillation in man: pronounced improvement with sequential pulse delivery to two different orientations," *Circulation*, vol. 73 · 3, pp. 484–491, Mar. 1986.

CF Babbs and SJ Whistler, "Evaluation of the operating internal resistance, inductance, and capacitance of intact damped sine wave defibrillators," *Medical Instrum.*, vol. 12 3 1, pp. 34–37, Jan.–Feb. 1978.

LA Geddes and WA Tacker, "Engineering and physiological considerations of direct capacitor-discharge ventricular defibrillation," *Med and Biol Eng.*, vol. 9, pp. 185–199, 1971.

PA Rubio and EM Farrell, "Low–Energy direct defibrillation of the human heart," vol. pp. 32–33, 1978.

CF Dahl, GA Ewy, ED Warner, et al, "Myocardial necrosis from direct current countershock: effect of paddle electrode size and time interval between discharges," *Circulation*, vol. 50, p. 956, 1974.

Feeser et al., Circulation, vol. 82, No. 6, (1990).

R.C. Balagot, et al. J. Thoracic and Cardiovasc Surgery, vol. 47 No. 4, pp. 487–504.

P.S. Chen et al., Circulation, vol. 73 No. 5 pp. 102–1028 (1986).

RS MacKay and SE Leeds, "Physiological effects of condenser discharges with application to tissue stimulation and ventricular defibrillation," *J Applies Physiology*, vol. 6, pp. 67–75, Jul. 1953.

WB Kouwenhoven and WR Milnor, "Treatment of ventricular fibrillation using a capacitor discharge," *J Applies Physiology*, vol. 7, pp. 253–257, Nov. 1957.

JL Prevost and F Batelli, "Sur quelques effets des descharges electriques sur le cour des mammifer, " *Comptes rendus hebdomadaires des séances de l'Académie des sciences*, vol. 129, pp. 1267, 1899.

RA Winkle, RH Mead, MA Ruder, et al., "Long–term outcome with the implantable cardioverter–defibrillator," *J Am Coll Cardiol.*, vol. 13, pp. 1353–, 1989.

MH Lehman, S Saksena, "Implantable cardioverter–defibrillators in cardiovascular practice: Report of the policy conference of the North American society of Pacing and Electrophysiology," PACE, vol. 14, pp. 969–979, Jun. 1991.

RA Winkle, "State–of–the –Art of the AICD," PACE, vol. 14, pp. 961–966, May 1991 pt II.

NG Tullo, S Saksena, RB Krol, "Technological improvements in future implantable defibrillators," CARDIO, vol. , pp. 107–111, May 1990.

DP Zipes, J Fischer, RM King, et al, "Termination of ventricular fibrillation in dogs by depolarizing a critical amount of myocardium," *Am J Cardiol.*, vol. 36, pp. 37–44, Jul. 1975.

AC Guyton and J Satterfield, "Factors concerned in defibrillation of the heart, particularly through the unopened chest," *Am J of Physiology*, vol. 167, pp. 81, 1951.

JC Schuder, GA Rahmoeller, and H Stoeckle, "Transthoracic ventricular defibrillation with triangular and trapezoidal waveforms," *Circ Res*, vol. 19, pp. 689–694, Oct. 1966.

WA Tacker, LA Geddes, J McFarlane, et al, "Optimum current duration for capacitor–discharge defibrillation of canine ventricles," *J Applied Physiology*, vol. 27 # 4, pp. 480–483, Oct. 1969.

JC Schuder, H Stoeckle, JA Wes, et al, "Transthoracic ventricular defibrillation in the dog with truncated and untruncated exponential stimuli,"*IEEE Trans. Biom. Eng.*, vol. BME–18 # 6, pp. 410–415, Nov. 1971.

G Weiss, "Sur la possibilite de rendre comparable entre eux les appareills survant a l'excitation electrique," *Arch. Ital. de Biol.*, vol. 35, pp. 413–446, 1901.

L Lapicque, "Definition experimentalle de l'excitabilite," *Proc. Soc. de Biol.*, vol. 77, pp. 280–285, 1909.

IMPLANTABLE DEFIBRILLATOR HAVING MULTIPLE PATHWAYS

CROSS-REFERENCES TO CO-PENDING APPLICATIONS

This application is a division of application 08/231,036 filed Apr. 22, 1994, now U.S. Pat. No. 5,514,160, which in turn is a division of application Ser. No. 07/841,544 filed Feb. 26, 1992, now U.S. Pat. No. 5,306,291. This application is also related to application Ser. No. 07/704,619 filed May 23, 1991, entitled "Implantable Defibrillator System Employing Switching Capacitor Networks", now U.S. Pat. No. 5,199,429, and also related to application Ser. No. 07/808,722, filed Dec. 17, 1991, entitled "Small Capacitance Defibrillation Process".

BACKGROUND OF THE INVENTION

1. Field of the Invention

The present invention relates generally to defibrillation methods, and more particularly, to implantable defibrillation systems for optimizing the efficiency thereof by steering energy and current.

2. Description of the Prior Art

Defibrillation, or causing the cessation of chaotic and uncoordinated contraction of the ventricular myocardium by application of an electrical voltage and current, in its most primitive form goes back to the last century. [J. L. Prevost and F. Batelli, "Sur Quelques Effets des Descharges Electriques su le Couer des Mammifers", *Comptes Rendus Hebdomadaires des Seances de L'Acadmie des Sciences*, Vol. 129, p. 1267, 1899.] The sophistication and effectiveness of defibrillation techniques has grown rapidly in subsequent decades. One of the most recent developments has been the practical advent of implantable defibrillation systems. [R. A. Winkle, et al., "Long-term Outcome with the Implantable Cardioverter-Defibrillator", *J. Am. Coll. Cardiol.*, Vol. 13, p. 1353, 1989; M. H. Lehman and S. Saksena, "Implantable Cardioverter-Defibrillators in Cardiovascular Practice: Report of the Policy Conference of the North American Society of Pacing and Electrophysiology", *PACE*, Vol. 14, p. 107, May, 1990.] With the acceptance of this technology, the new challenge is to reduce system size while preserving its effectiveness, in order to improve the patient's quality of life and to extend the range of application of such systems. [R. A. Winkle, "State of the Art of the AICD", *PACE*, Vol. 14, p. 961, May, 1991, Part II; N. G. Tullo, S. Saksena and R. B. Krol, "Technological Improvements in Future Implantable Defibrillators", *CARDIO*, Vol. 13, p. 197, May, 1990.]

Until an ability to anticipate fibrillation has been achieved, it will be necessary to achieve defibrillation by passing a large current through the heart. The current must he large enough to depolarize a large fraction of the myocardium, thus extinguishing depolarization wavefronts. [D. P. Zipes, et al., "Termination of Ventricular Fibrillation in Dogs by Depolarizing a Critical Amount of Myocardium", *Am. J. Cardiol.*, Vol. 36, p. 37, July, 1975.]

The high values of current that are employed generally in defibrillation procedures and the compactness that is essential in implantable systems are conflicting requirements. For this reason, a huge premium is placed on optimal delivery of the current and energy necessary for successful defibrillation. But, with the kinds of defibrillation electrodes that are most conveniently employed, the energy distribution or "steering" that occurs naturally departs significantly from the optimum. The present invention provides steering methods that improve the pattern of energy delivery when the simplest and least costly electrode systems are used.

Figure 1A:
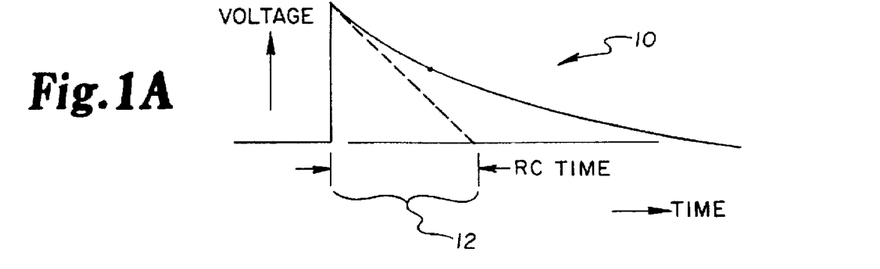
FIG. 1A illustrates the voltage-time waveform of a capacitor discharged through a resistor.

For reasons of simplicity and compactness, capacitor-discharge systems are almost universally used in defibrillation. Achieving the requisite electric field needed to depolarize most of the myocardial cells requires current density above a certain threshold value, and via Ohm's law, this means the process is favored by achieving sufficiently low electrical resistance in the discharge path. For this reason, the use of electrodes of relatively large surface area has for a long time been the norm. [A. C. Guyton and J. Satterfield, "Factors Concerned in Defibrillation of the Heart, Particularly through the Unopened Chest", *Am. J. of Physiology*, Vol. 167, p. 81, 1951.] The discharge of a capacitor C through a fixed resistance R results in a voltage-versus-time curve (and hence, current versus time as well) that is a declining exponential, with a characteristic time given by the product RC, as illustrated in FIG. 1A. Although the heart does not constitute a "fixed" resistor (that is, does not have a linear current-voltage characteristic) the assumption of its linearity yields a useful qualitative description of defibrillation electrical events, and will be used in the explanations that follow.

It has also been recognized for some time, however, that the low-voltage (and low-current) "tail" of the capacitor-discharge pulse is detrimental. [J. C. Schuder, G. A. Rahmoeller and H. Stoeckle, "Transthoracic Ventricular Defibrillation with Triangular and Trapezoidal Waveforms", *Circ. Res.*, Vol. 19, p. 689, October, 1966; W. A. Tacker, et al., "Optimum Current Duration for Capacitor-Discharge Defibrillation of Canine Ventricles", *J. Applied Physiology*, Vol. 27, p. 480, October, 1969.]The exact reason for this detrimental effect is not known, although plausible speculations exist.

Figure 1B:
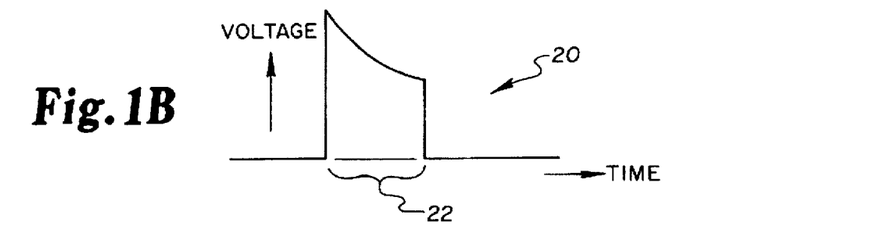
FIG. 1B illustrates the voltage-time waveform of a monophasic pulse, produced by discharging a capacitor through a resistor and terminating the pulse by switching.

For this reason, most efforts have been directed at time-truncated capacitor discharges, as illustrated in FIG. 1B. [J. C. Schuder, et al., "Transthoracic Ventricular Defibrillation in the Dog with Truncated and Untruncated Exponential Stimuli", *IEEE Trans Biom. Eng.*, Vol. BME-18, p. 410, November, 1971.] That is, the capacitor discharge is simply interrupted by opening a switch at some middle point, typically, approximately at the time that the characteristic "RC time" has been reached. The advent of compact solid-state switches has made such pulse tailoring a straightforward matter. The truncated capacitance-discharge pulse shown in FIG. 1B is known as the monophasic waveform of the prior art. An important variation on the pulse shape is the biphasic waveform of FIG. 1C, wherein the pulse is extended, but with reversed polarity, again through a switching technique.

Figure 2:
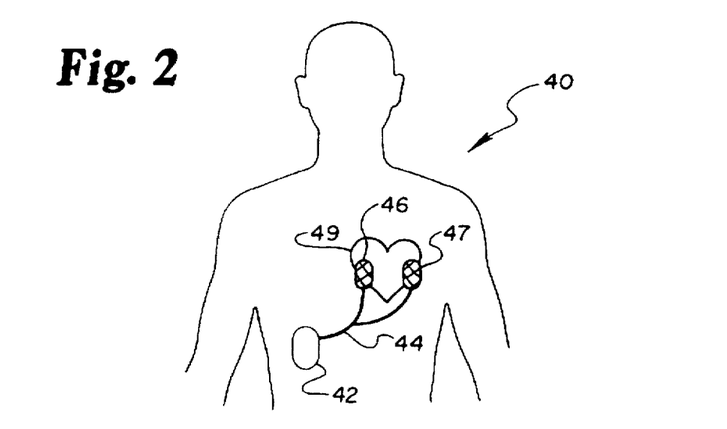
FIG. 2 illustrates schematically a defibrillation system comprising an abdominally implanted pulse generator and attached to two epicardial-patch electrodes.

Now turn to the electrodes used to deliver current to the cardiac muscle. Among the most efficient are epicardial-patch electrodes 46 and 47, which are relatively large-area flexible conductive elements that are stitched directly to the epicardium, or exterior of the heart 49, as illustrated in FIG. 2. The obvious shortcoming of this method is, of course, that it requires major surgery and invokes the hazards of opening the chest cavity for attachment of the patches.

An appreciably simpler option positions an endocardial coil electrode 62 at the right ventricular apex (RVA) 64, or the lowest point inside the right ventricle 66. This usually takes the form of a helix or coil, fabricated from metal, ribbon or wire, wound on the exterior of a cardiac catheter 60 that is introduced intravenously. This option is illustrated in the lower-left hand portion of FIG. 3. Since the catheter can be used for other purposes, such as pacing, as well, the simple addition of an electrode to it is an attractive feature of this option. Even more important, the surgery needed for the use of epicardial patches is avoided. And since it is ventricular tissue that requires electrical treatment for successful defibrillation, such an RVA electrode 62 is quite strategically positioned for the purpose. A second electrode is also needed, of course, to accompany the RVA electrode. An option that is often used is the subcutaneous patch 54 (hereinafter abbreviated as "SUB"). It is a relatively large-area element, illustrated schematically in the lower-right portion of FIG. 3 (where distances are not represented to scale), that is positioned under the skin of the left chest. Thus, current passed from SUB 54 to RVA 62 intersects virtually all of the ventricular tissue, as desired. The SUB 54 option has the shortcoming that the patch, as a shallow implant, is vulnerable to damage from bumps and other mishaps, and even from normal bodily motion, but it has the major advantage that open-chest surgery is again avoided.

A promising alternative (for augmentation) to the SUB electrode is using the metal housing or CAN 52 (as hereinafter designated) of the defibrillation pulse-generator module 57 as an electrode, an option that is the subject of a co-pending application now issued as U.S. Pat. No. 5,199,429. This option is especially attractive because CAN 52 is mechanically stronger than SUB 54, and hence is not liable to breakage, and also because CAN 52 must be implanted in any case. The CAN option is illustrated schematically in the upper-right portion of FIG. 3. This use of the pulse generator itself brings the proviso, however, that CAN 52 must be small enough for pectoral implantation without serious comfort or cosmetic compromises. The larger implantable pulse generators of the prior art have been placed in the comparatively spacious abdominal cavity. But abdominal placement does not permit use of the CAN electrode concept; the current path is too long for efficiency, and also the discharge would result in extreme discomfort. Further, the current vector intersects the heart disadvantageously. Thus, a further premium and benefit is derived from a size reduction of the pulse generator that permits pectoral implantation, and the efficiency improvement inherent in the present invention is aimed at precisely such a size reduction.

A fourth electrode option that is comparatively easy to realize is simply a second endocardial coil added to a catheter that already carries the RVA electrode. [M. Mirowski, U.S. Pat. No. 3,942,536, 1976]. It is a straight-forward matter to position this second coil electrode 68 in the superior vena cava 70 (SVC hereinafter), the chamber immediately above the right atrium 72, as illustrated in the upper-left portion of FIG. 3. The right atrium itself is sometimes chosen as the location, and an appreciably more difficult-to-reach location, the coronary sinus, is also sometimes chosen. But since these three sites are proximate, we shall simplify the following descriptions by using the SVC designation only to stand for any electrode in this region of the heart.

SUMMARY OF THE INVENTION

Figure 3:
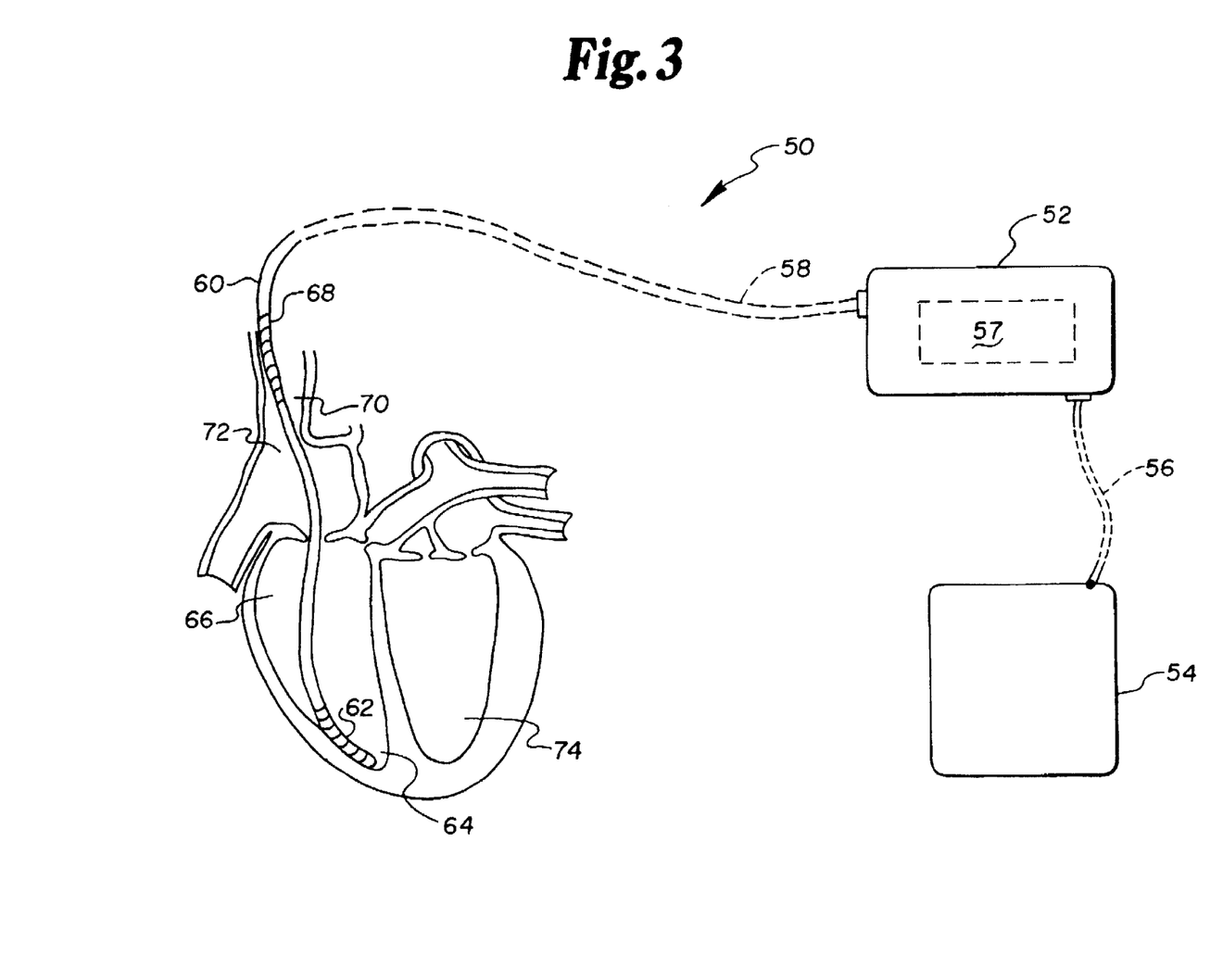
FIG. 3 illustrates schematically a defibrillation system comprising a pectorally implanted pulse generator serving as CAN electrode, and attached to two endocardial-coil electrodes, SVC and RVA, and one subcutaneously implanted SUB electrode.

Three prior-art electrode options and one that is the subject of a co-pending application have just been described, all of them requiring substantially less hazard and trauma for the patient than do epicardial-patch electrodes. In a schematic way, FIG. 3 shows the relationships of all four of these electrodes that are comparatively easy to implant. It is evident, now, that several choices of electrode interconnections and polarities exist for applying the defibrillation waveform.

In a common and typical defibrillation method, only the RVA, SVC, and SUB electrodes are present. Similarly typical is the "RVA [as] cathode" discharge. In the monophasic case, the positive potential is usually applied to the SVC and SUB electrodes in common. Having the SVC and RVA electrodes common and negative has been found ineffective, and is usually avoided. Also, when the fourth or CAN electrode is present in addition to the other three, it is standard practice to let SUB and CAN be common; to do otherwise would cause a local current in the left chest that would scarcely intersect the heart. Thus, it is that the path and polarity options that at first glance appear to be numerous are reduced by practical and elementary considerations to a considerably smaller number.

Return now to the case of three electrodes, for which relevant data can be drawn from the literature. It has been reported that in the canine heart, the SVC-RVA pathway presents a resistance of 75 ohms, and the RVA-SUB pathway, 103 ohms. [J. N. Wetherbee, et al., "Sequential Shocks are Comparable to Single Shocks Employing Two Current Pathways for Internal Defibrillation in Dogs", *PACE*, Vol. 11, p. 696, June, 1988.] Thus, when the SVC and SUB electrodes are made common, the first-named pathway will carry the larger current. This causes problems: First, the top-down current is not as effective as an equal "horizontal" current would be, one passing through much of the ventricular myocardium. Second, the SVC electrode typically makes a small-area contact with the cardiac tissue, and the resulting locally high value of current density can cause tissue damage. Evidence of the first assertion is the observation that the three-electrode option is at best marginally more effective for defibrillation than the two-electrode option, RVA and SUB only. [J. N. Wetherbee, et al., "Nonthoracotomy Internal Defibrillation in Dogs: Threshold Reduction Using a Subcutaneous Chest Wall Electrode with a Transvenous Catheter Electrode", *J. Am. Coll. Cardiol.*, Vol. 10, p. 406, August, 1987.

It is clear that a CAN electrode of the co-pending application may be used in lieu of SUB, and that this would yield a comparable physical and electrical situation. Note, however, that combining CAN and SUB in parallel will produce an improvement by reducing resistance in the "horizontal" pathway, thereby rendering the vertical and horizontal currents more nearly equal. But it is still desirable, whether one or two left-chest electrodes are used, to diminish the wasted current and energy in the SVC-RVA pathway, to reduce tissue damage at the same time, and still to retain whatever defibrillation benefit can be derived from the diminished current in this path, since the SVC electrode is available at small incremental cost.

From a current value well above the defibrillation threshold, the reaction of cells depolarized diminishes as current is reduced, but diminishes more slowly than current, thus improving the fractional incremental benefit. Current reduction obviously will reduce the problem of tissue damage. Also, because defibrillation uses a transient waveform, rather than a static current and voltage, a second approach to reducing local tissue damage is to reduce energy delivered. Thus, there are at least two variables, current and energy, that can be adjusted to achieve more favorable discharge steering, or distribution of power dissipation, the aim of the present invention.

Let energy reduction in the SVC-RVA pathway be the first method described. In order to simplify descriptive analysis (which is in any case only qualitative), assume that resistance in the SVC-RVA route equals that in the SUB-RVA route. The latter may of course involve the SUB and CAN electrodes in parallel, which makes the assumption more accurate, but for simplicity, the designation "SUB" will be used below for either case. To reduce energy absorbed in the SVC-RVA pathway, exploit modern switching technology again to apply the discharge voltage to the SVC electrode at some time after it has been applied to the SUB electrode, and then terminate the voltage to both electrodes simultaneously. The circuit illustrated schematically in FIG. 4 accomplishes this result. The switch 96 is programmable by the physician to close (as typical examples) 1, 2, 3, 4, 5, or 6 milliseconds after the switch 100 that delivers the primary waveform.

In representative cases, the duration of the SVC waveform might be 40% to 60% that of the SUB waveform. This arrangement will cause a major fraction of the discharge energy to flow from SUB to RVA, and an example of the resulting monophasic waveform is illustrated in FIG. 5A. For the given assumptions, the characteristic time (RC time) of the system is cut in half by placing SUB and SVC in parallel, with the resulting factor-of-two change of slope in the waveform that is displayed in FIG. 5A. It should also be noted that this arrangement automatically reduces peak voltage, and hence peak current and peak field in the tissue, in the path of the briefer pulse, which is displayed in FIG. 5B. But it is obvious, of course, that the smaller-duration waveform could be shifted to an earlier time, in the limit having the same peak voltage as the waveform applied to SUB. Such variations are produced by altering the operation timing of switches 96 and 100 in FIG. 4.

The duration of a defibrillating pulse is another variable that is not related linearly to pulse effectiveness, with pulses of 2 to 3 milliseconds having been shown to be useful. This relates to a characteristic time of the heart known as chronaxie. [L. Lapicque, "Definition Experimentelle de l'excitabilite", Proc. Soc. deBiol., Vol. 77, p. 280, 1909; G. Weiss, "Sur la Possibilite de Rendre Comparable entre Eux les Appareils Suivant a l'Excitation Electrique", Arch. Ital, deBiol., Vol. 35, p. 413, 1901.] Typical values of chronaxie are indeed between 2 and 3 milliseconds, and the effectiveness of pulses of such length is exploited in another copending application. [T. Adams, M. Kroll, "Small-Capacitance Defibrillation Process", U.S. Patent application Ser. No. 07/808,722]. Finally, the same pulse-delay principle is applicable to the bipbasic waveform, with the primary-pulse result shown in FIG. 5C, and the shorter-pulse result, in FIG. 5D.

The manipulation of pulse duration is only one of several methods for altering energy distribution between two discharge paths, or among more than two. It is also possible to reduce the voltage delivered to one electrode as compared to another. (Let us adhere to the case of three electrodes, RVA 62, SVC 68, and SUB 54, since this case fully illustrates the principles.) A simple way to achieve this result is by placing a lossy element in series in the path where lower voltage and current are desired.

Still another approach exploits capacitor-switching techniques, such as charging capacitors in series and discharging them in parallel. Somewhat nonobviously, the use of "lossy" components yields a more efficient result than this simple switching method, however, because the energy stored in a charged capacitor has a square-law dependence on voltage. Efficiency improvements in a co-pending application that employs capacitor switching, are brought about by the capturing of energy otherwise wasted now issued as U.S. Pat. No. 5,199,429.

To illustrate the principles involved in the several options, numerical examples employing typical values are helpful.

For still greater clarity, let the examples be further simplified by considering these options as applied to a single conducting path. The extension to multiple-path cases will be obvious. As representative values, let us choose C=100 uF, a number that plays a dominant role in determining the physical volume of the pulse generator, and hence choice of implantation site. Let the high-voltage power supply deliver 700 volts, a realistic value, and let the resistance of the defibrillation pathway be taken as 70 ohms. These values lead to an RC time constant of 7 milliseconds. If the pulse were truncated at the RC time, its voltage amplitude would be 0.37 of the initial value. Let us instead, however, truncate the pulse at the point where its amplitude is half its original value, a choice that simplifies energy relationships. This yields a pulse duration of 4.85 ms rather than 7 ms.

Figure 6A:
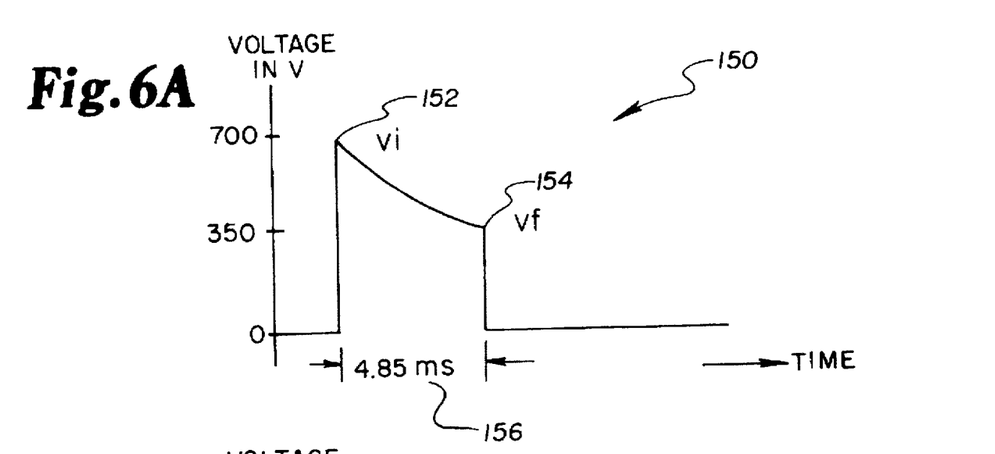
FIG. 6A illustrates the voltage-time waveform of a particular monophasic pulse for analytic comparison.

To establish a benchmark for comparing the options, first consider the 100-uF capacitor to be charged in the initial voltage $V_i=700$ V, for a stored energy of 24.5J. If delivered in a monophasic pulse that is terminated at $V_f=350$ V as illustrated in FIG. 6A, then one-quarter of this energy (via the square law) remains unused in the capacitor and the balance, 18.4J, is delivered to the defibrillation path.

Now, to examine the capacitor-switching option, let two 50-uF capacitors be charged in series to 700V. Switching at the time of discharge to a parallel interconnection yields 100 uF of capacitance charged to $V_i=350$V, for an initial storage of 6.125J. If the pulse is terminated once more at half voltage (as in FIG. 6B), or at $V_f=175$V, then the energy delivered to the defibrillation path is 4.59J.

Next, let a 70-ohm resistor $R_3$ be placed in series in the discharge path. It is evident that equal amounts of energy will be dissipated in the resistor $R_3$ and in the equal defibrillation-path resistance R. This is illustrated in FIG. 6C, where the upper trace constitutes the waveform delivered to the two resistances in series, and the lower trace, the waveform delivered to the defibrillation path. Because the RC time has been doubled in this case, twice the time is necessary for the respective voltages to fall to half their initial values. If this pulse duration is acceptable, one-quarter of the energy remains stored in the capacitor at the termination of the pulse, as was the case in FIGS. 6A and 6B. But three-eighths of the energy stored initially, or 9.19J, is delivered to the defibrillation path this time, or twice as much as in the capacitance-switching option.

If, on the other hand, it is desired to terminate the pulse at the same absolute time as in the two preceding examples, then the voltage amplitude is 0.707 of the initial value, so that the energy remains in the capacitor is half that initially stored. Each resistor dissipates one-quarter of the initial energy, which is to say that 6.125J is delivered to the defibrillation path. To conclude this discussion of a resistor as the lossy device, note that the method is as readily applicable to the biphasic as to the monophasic waveform.

Another lossy-device option is the "current limiter". This term usually identifies a two-terminal current-regulating device of a kind that has been known in the semiconductor art since the latter 1950s. From the early 1950s it has been possible to accomplish a similar result by using three-terminal devices, and hence somewhat more complicated circuitry. The simplest realization of a two-terminal current limiter is a depletion-mode field-effect transistor, either JFET or MOSFET, with source and drain being the two relevant terminals. Field-effect transistors with characteristic currents above an ampere have been fabricated since the 1960s, and are useful as switches in the defibrillation art.

Figure 7A:
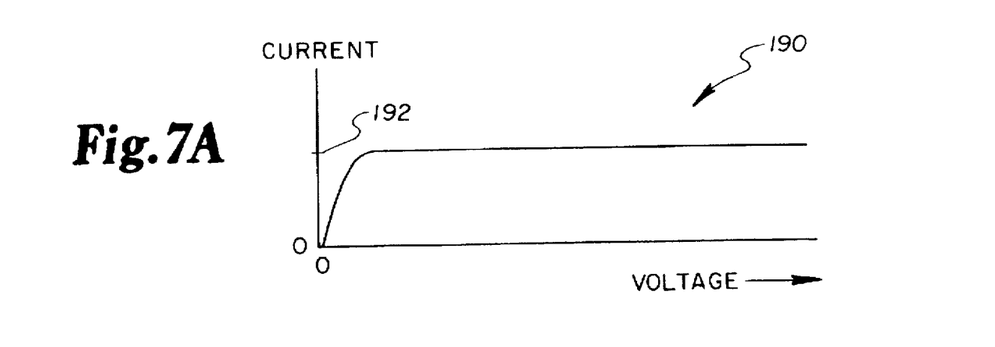
FIG. 7A illustrates the current-voltage characteristic of a particular current limiter placed in series with a particular resistor.
Figure 7B:
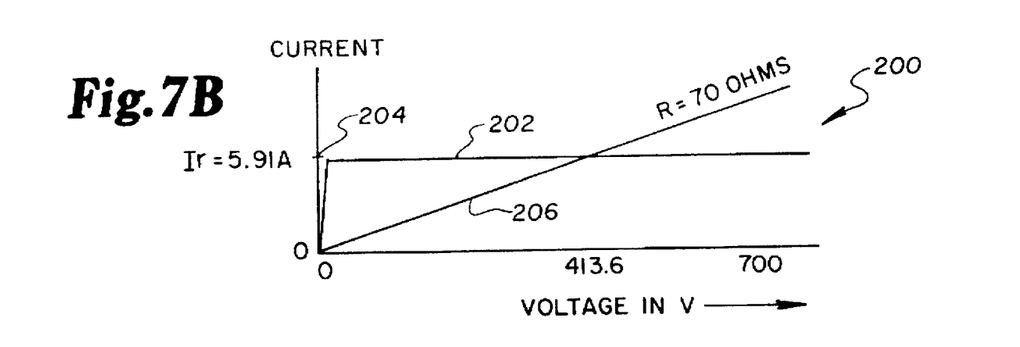
FIG. 7B illustrates a comparison of an idealized current-voltage characteristic for a current limiter with a characteristic current superimposed upon the current-voltage characteristic of a resistance.
Figure 7C:
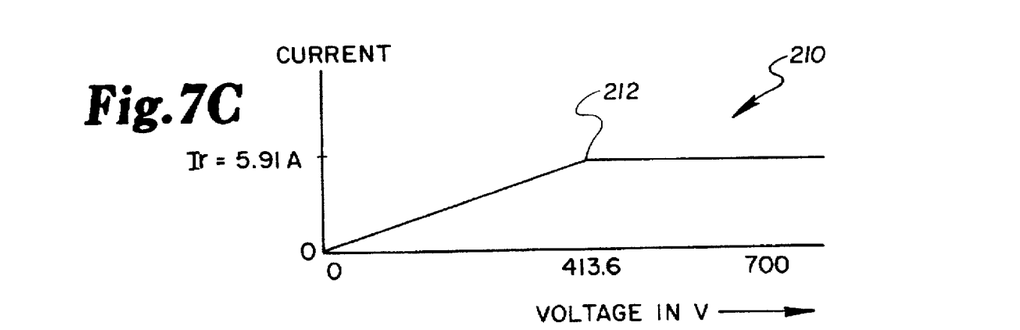
FIG. 7C illustrates a composite current-voltage characteristic of the particular idealized current limiter shown in FIG. 7B.

The current-voltage characteristic of a current limiter is shown in FIG. 7A. In FIG. 7B, the current-limiter I-V characteristic is idealized somewhat and superimposed on that of the defibrillation path, taken to be the 70-ohm fixed resistor R. Placing the defibrillation path and current limiter in series yields the composite I–V characteristic presented in FIG. 7C. The aim at this point is to determine the maximum regulated current $I_r$ that permits capacitor voltage to fall from its initial value, $V_i$=700 V, to a final value that imposes a rectangular current waveform and rectangular voltage waveform on the defibrillation path, a case that yields a particularly clear view of the behavior of a current-limiter circuit. Action of the current limiter drains the capacitor at a constant rate; yielding a linear ramp of negative slope, rather than the familiar declining-exponential waveform. Thus, what is needed is a value for the final voltage $V_f$ that is just sufficient to drive the highest possible regulated current $I_r$ through the resistance R=70 ohms of the defibrillation path, a voltage given by Ohm's law as:

$$V_f = I_r R \qquad \text{Eq. 1}$$

(At the conclusion of the pulse, the idealized current limiter displays zero resistance, so only R remains in the circuit.) Further, the voltage change $V_i - V_f$ must be consistent with the charge increment Q drawn from the capacitor during the pulse, a quantity given by:

$$\Delta Q = I_r \Delta t \qquad \text{Eq. 2}$$

Eliminating $I_r$ from Eqs. 1 and 2 yields:

$$V_f = R(\Delta Q/\Delta t) \qquad \text{Eq. 3}$$

But from the capacitor law, $$\Delta Q = C(V_i - V_f) \qquad \text{Eq. 4}$$

Eliminating $V_f$ from Eqs. 3 and 4 gives:

$$\begin{aligned}\Delta Q &= V_i/[(R/\Delta t) - (1/C)] \qquad \text{Eq. 5}\\ &= (700 \text{ V})/\{(70 \text{ Ohm})/(4.85 \times 10^{-3} s)] - (1/10^{-4} F)\}\\ &= 0.02865 \, C\end{aligned}$$

Thus, from Eq. 2, $$I_r = (\Delta Q/\Delta t) = 5.91 A \qquad \text{Eq. 6}$$

and from Eq. 1, $$V_f = (5.91 \text{ A})(70 \text{ ohm}) = 413.6 \text{ V} \qquad \text{Eq. 7}$$

Figure 7D:
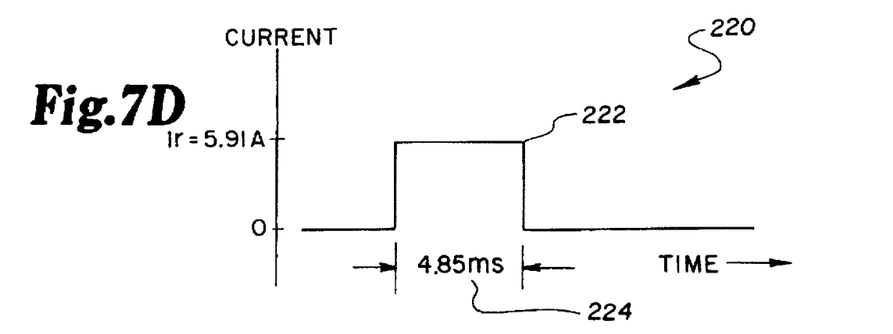
FIG. 7D illustrates the rectangular current-time waveform of a particular monophasic pulse achieved by using a current limiter.

It follows that choosing a current limiter with a characteristic current of $I_r$=5.91A will deliver a rectangular current waveform as illustrated in FIG. 7D. The accompanying voltage waveform is shown as the lower trace in FIG. 7E, while the voltage waveform on R and current limiter in series is the upper trace.

It is evident that the energy delivered to the defibrillation path is:

$$\begin{aligned}\text{Energy} &= I_r^2 R \Delta t = (5.91 A)^2 (70 \text{ ohm}) \qquad \text{Eq. 8}\\ &\quad (4.85 \times 10^{-3} s)\\ &= 11.9 J\end{aligned}$$

With $V_f$ being larger than before, a larger fraction of the energy initially stored is left in the capacitor this time, namely 35% , or 6.4J. Thus, the current-limiter technique is applicable to single-path defibrillation discharges for generating more nearly rectangular waveforms, as well as to the combined purposes of steering energy in the case of multiple paths and achieving rectangular waveforms in such a case as well.

To summarize, for the standardized (1) capacitance, (2) initial voltage available, and (3) pulse duration, that were chosen above, the current-limiter method delivers 65% as much energy to the defibrillation path as does a conventional monophasic waveform generated without lossy elements. (The reason for this good performance is that the grossly nonlinear current limiter "looks like" a small and declining resistance to the capacitor, with an effective value for the case of the idealized current limiter that goes from 48 ohms to zero during the course of the particular pulse of the example.) The resistor $R_3$ matching defibrillation-path resistance R permits 33% as much energy to be delivered to the defibrillation path as does the monophasic pulse of equal duration. And, the capacitance-switching method delivers 25% of the energy delivered by the monophasic pulse.

As a final point, it should be noted that the current-limiter method is applicable to the biphasic option as well as the monophasic. A JFET with floating gate displays the I–V characteristic shown in FIG. 7F, and hence constitutes a bilaterally symmetric current limiter.

One significant aspect and feature of the present invention is the full use of electrodes that can be implanted by means of comparatively low-cost and low-risk methods, with examples being RVA, SVC, SUB, and CAN electrodes.

Another significant aspect and feature of the present invention is the steering of the energy of a defibrillation pulse to achieve a more favorable energy distribution than occurs naturally when such convenient electrodes are used.

Still another significant aspect and feature of the present invention is the steering of the current of a defibrillation pulse to achieve a more favorable current distribution than occurs naturally when such convenient electrodes are used.

Yet another significant aspect and feature of the present invention is the use of SUB and CAN electrodes in common to reduce the resistance in the resulting defibrillation pathway as compared to just one of the pathways.

Another significant aspect and feature of the present invention is the use of a lossy device in the SVC-RVA pathway to reduce current and energy therein.

Still another significant aspect and feature of the present invention is the use of a resistor in the SVC-RVA pathway to reduce current and energy therein.

Yet another significant aspect and feature of the present invention is the use of a current limiter in the SVC-RVA pathway to reduce current and energy therein.

Another significant aspect and feature of the present invention is the use of a smaller-duration pulse in the SVC-RVA pathway than in the SUB-RVA pathway or the CAN-RVA pathway, to reduce current and energy in the first pathway.

Still another significant aspect and feature of the present invention is using one or more current limiters in one or more defibrillation pathways to derive from a capacitor discharge rectangular current and voltage pulses in those pathways.

Having thus described the embodiments and features of the present invention, we note that it is a principal object of the invention to use the fullest effect electrodes that can be implanted by means of comparatively low-cost and low-risk methods, with examples being RVA, SVC, SUB, and CAN electrodes.

A further object of the present invention is the steering of the energy of a defibrillation pulse to achieve a more favorable energy distribution than occurs naturally when the most convenient electrodes are used.

A still further object of the present invention is the steering of the current of a defibrillation pulse to achieve a more favorable current distribution than occurs naturally when the most convenient electrodes are used.

Still another object of the present invention is to use the SUB and CAN electrodes in common to reduce the resistance in the resulting defibrillation pathway as compared to just one of the pathways.

A further object of the present invention is to reduce current and energy in the SVC-RVA pathway as compared to those values in other pathways.

A still further object of the present invention is to diminish tissue damage in the SVC-RVA pathway.

Yet a further object of the present invention is to derive from a capacitor discharge rectangular current and voltage pulses in one or more defibrillation pathways.

A still further object of the present invention is to improve the efficiency of an implantable defibrillation system.

Yet a further object of the present invention is to diminish the size of the pulse generator for an implantable defibrillation system having a given degree of defibrillation effectiveness.

A further object of the present invention is facilitating the pectoral implantation of the pulse generator for an implantable defibrillation system having a given degree of defibrillation effectiveness, in turn to permit taking advantage of the CAN electrode.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PRIOR ART

FIG. 1A illustrates the voltage-time waveform 10 of a capacitor discharged through a resistor, and waveform displaying the characteristic time 12 known as the RC time.

FIG. 1B illustrates the voltage-time waveform 20 of a monophasic pulse of the prior art, produced by discharging a capacitor through a resistor and terminating the pulse after a time 22 by switching.

Figure 1C:
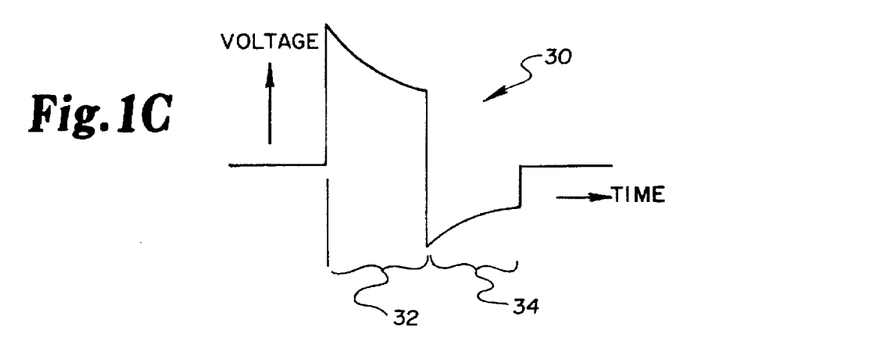
FIG. 1C illustrates the voltage-time waveform of a biphasic pulse, produced by discharging a capacitor through a resistor, reversing the polarity by switching, and terminating the pulse by further switching.

FIG. 1C illustrates the voltage-time waveform 30 of a biphasic pulse of the prior art, produced by discharging a capacitor through a resistor, reversing the polarity by switching after a time interval 32, and terminating the pulse after a further time interval 34 by further switching.

FIG. 2 illustrates schematically a patient 40 fitted with a defibrillation system comprising an abdominally implanted pulse generator 42, connected by means of electrical harness 44 to two epicardial-patch electrodes 46 and 47, which are attached to the heart 49 of the patient 40.

DESCRIPTION OF THE PREFERRED EMBODIMENTS

FIG. 3 illustrates schematically and for purposes of illustration a defibrillation system 50 including a pectorally implanted pulse generator 57 serving as a CAN electrode 52, the pulse generator 57 attached to a subcutaneously implanted SUB electrode 54 by interconnection 56, and by interconnection 58 to a cardiac catheter 60 that includes a first endocardial-coil electrode 62 positioned at the, apex 64 of the right ventricle 66, the coil being the RVA electrode 62, and a second endocardial-coil electrode 68 positioned in the superior vena cava 70, which is above the right atrium 72, the second coil being the SVC electrode 68, a configuration that causes defibrillation current coming from the CAN electrode 52 and coming from the SUB electrode 54 substantially to intersect the left ventricle 74, as well as the right ventricle 66. The methods of the present invention reduce defibrillation current and energy delivered to the path from the SVC electrode 68 to the RVA electrode 62.

Figure 4:
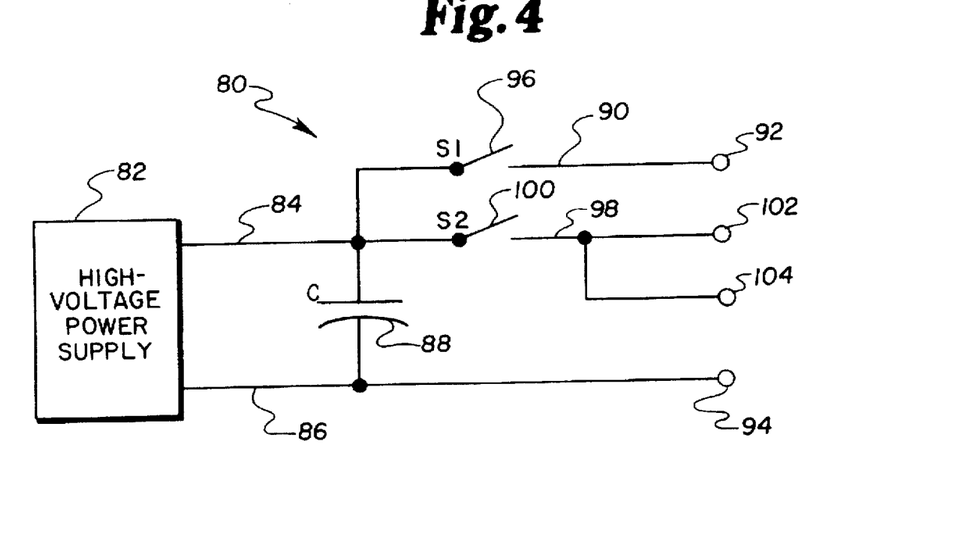
FIG. 4 illustrates schematically a pulse-generator configuration for an implantable defibrillation system, said configuration comprising a high-voltage power supply, a capacitor to be discharged, and switches to govern the delivery of energy to terminals to be connected to two to four electrodes.
Figure 5A:
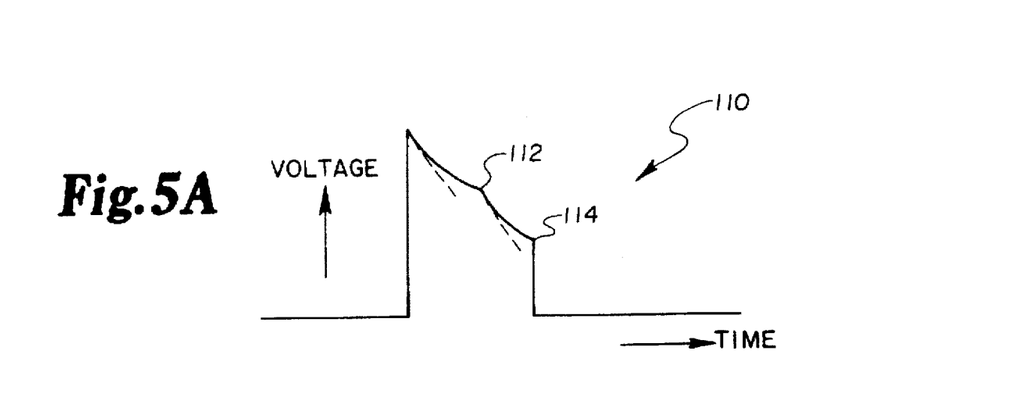
FIG. 5A illustrates the voltage-time waveform of a monophasic pulse, produced by discharging a capacitor through one or more paths initially, and placing an additional path in parallel therewith during the course of the pulse, and terminating current through all paths simultaneously by switching.

FIG. 4 illustrates schematically a pulse-generator configuration 80 for an implantable defibrillation system, the configuration comprising a high-voltage power supply 82, having first and second output leads 84 and 86 for charging a capacitor 88, the capacitor to be discharged through at least one of two paths, where the first path 90 is completed through chest tissue from an SVC electrode 68 that is connected to a first terminal 92, to an RVA electrode 62 that is connected to a second terminal 94 that is in turn connected to the second output lead 86, the first path 90 being under the control of a first single-pole, single-throw, switch 96, and where the second path 98 is under the control of a second single-pole, single-throw switch 100, and where said second path 98 is completed through chest tissue from electrically common SUB and CAN electrodes 54 and 52 that are respectively connected to a third terminal 102 and a fourth terminal 104, again to the RVA electrode 62 that is connected to the second terminal 94 with the present invention adjusting the current and energy delivered through the first path 90 by at least one method of, first, having the first switch 96 closed for a shorter time than the second switch 100, and second, placing a lossy component in series in the first path 90.

FIG. 5A illustrates the voltage-time waveform 110 of a monophasic pulse produced by discharging a capacitor through one or more paths initially, and placing an additional path in parallel therewith during the course of the pulse at the time 112, and terminating current through all paths simultaneously by switching at the time 114.

Figure 5B:
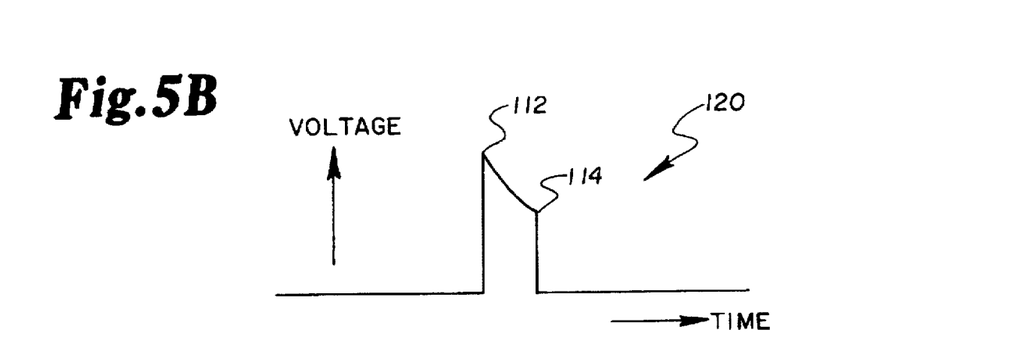
FIG. 5B illustrates the voltage-time waveform received by the additional path in the description of FIG. 5A.

FIG. 5B illustrates the voltage-time waveform 120 received by the additional path in the description of FIG. 5A, a waveform that results from closing the switches in the additional path at the time 112, and terminating current through the path at the time 114 where all numerals correspond to those elements previously described.

Figure 5C:
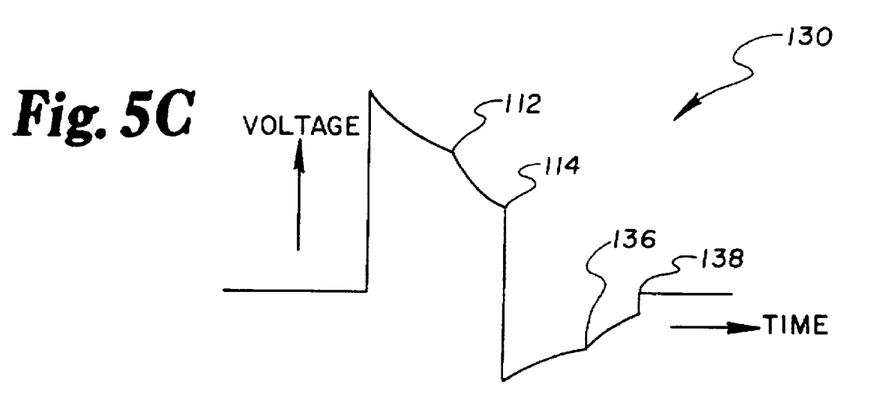
FIG. 5C illustrates the voltage-time waveform of a biphasic pulse, produced by the method in the description of FIG. 5A, but with the addition of polarity reversal by switching in lieu of pulse termination, of again placing the additional path in parallel with the primary path during the course of the reversed-polarity pulse, and then terminating current through all paths simultaneously by switching.

FIG. 5C illustrates the voltage-time waveform 130 of a biphasic pulse, produced by the method in the description of FIG. 5A, but with the addition of polarity reversal by switching at the time 114 in lieu of pulse termination, of again placing the additional path in parallel with the primary path at the time 136 during the course of the reversed-polarity pulse, and then terminating current through all paths simultaneously by switching at time 138 where all numerals correspond to those elements previously described.

Figure 5D:
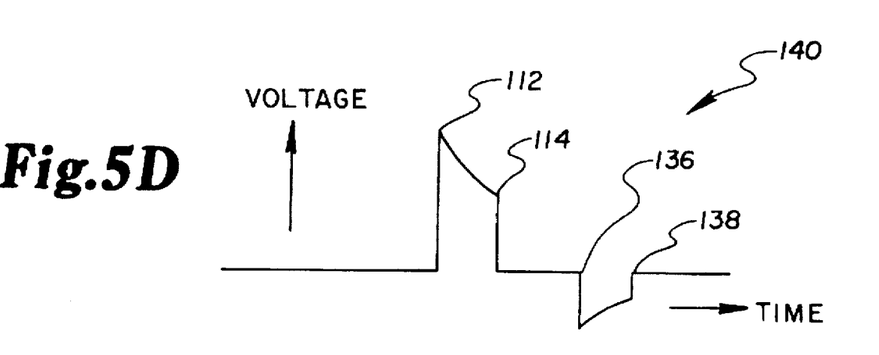
FIG. 5D illustrates the voltage-time waveform received by the additional path in the description of FIG. 5C.

FIG. 5D illustrates the voltage-time waveform received by the additional path in the description of FIG. 5C, wherein the additional path is placed in parallel with the primary path at the time 136 during the course of the reversed-polarity pulse, and then current through all paths is terminated simultaneously by switching at time 138 where all numerals correspond to those elements previously described.

FIG. 6A illustrates the voltage-time waveform 150 of a particular monophasic pulse for analytic comparison, comprising an initial voltage 152, a final voltage 154, and a pulse duration 156 where all numerals correspond to those elements previously described.

Figure 6B:
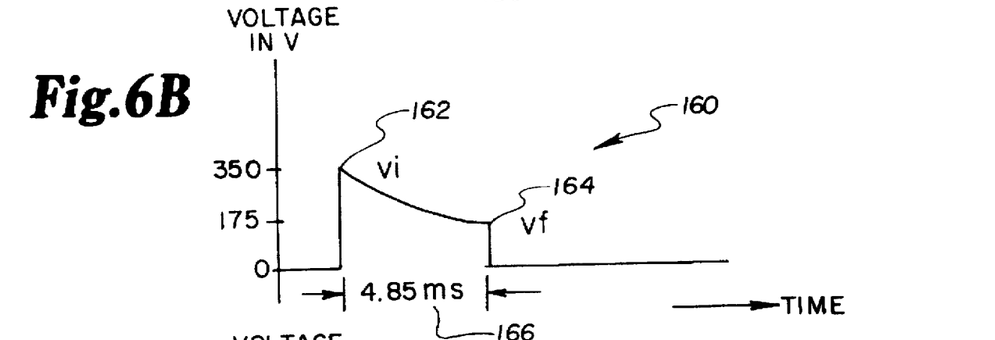
FIG. 6B illustrates the voltage-time waveform of a monophasic pulse produced by capacitor switching.
Figure 6C:
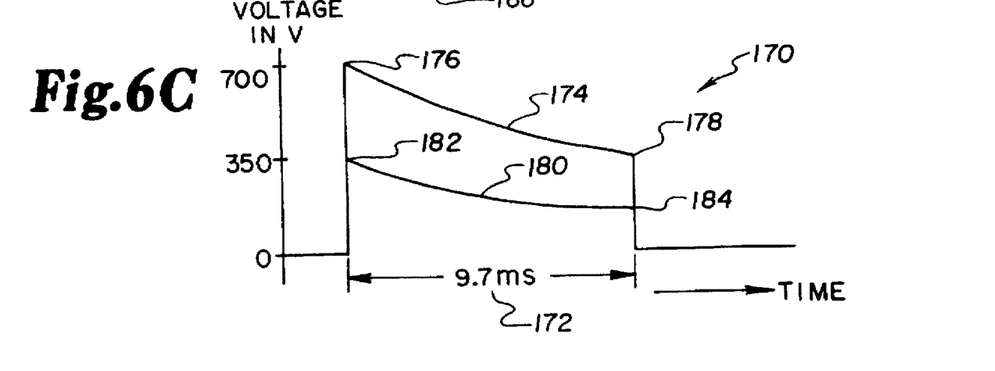
FIG. 6C illustrates the voltage-time waveform produced by doubling the resistance used in the case of FIG. 6A.

FIG. 6B illustrates the voltage-time waveform 160 of a monophasic pulse produced by capacitor switching, comprising an initial voltage 162, a final voltage 164, and a pulse duration 166 where all numerals correspond to those elements previously described.

FIG. 6C illustrates the voltage-time waveform 170 produced by doubling the resistance used in the case of FIG. 6A, the waveform 170 having a pulse duration 172, and comprising an upper trace 174 representing voltage on the two resistors in series, and having an initial voltage 176, a final voltage 178, and having a lower trace 180 representing voltage on the tissue resistor, and having an initial voltage 182, a final voltage 184 where all numerals correspond to those elements previously described.

FIG. 7A illustrates the current-voltage characteristic of a current limiter, having a characteristic current 192.

FIG. 7B illustrates a comparison 200 of an idealized current-voltage characteristic 202 for a particular current limiter with a characteristic current 204 superimposed upon current-voltage characteristic 206 of a resistor of 70 ohms where all numerals correspond to those elements previously described.

FIG. 7C illustrates the composite current-voltage characteristic 210 of the particular idealized current limiter 202 of FIG. 7B placed in series with the particular 70-ohm resistor 206 of FIG. 7B, displaying a "knee" 212 with coordinates 5.91A and 413.6V where all numerals correspond to those elements previously described.

FIG. 7D illustrates the rectangular current-time waveform 220 of a particular monophasic pulse having an amplitude 222 and a pulse duration 224, achieved by using a current limiter, where all numerals correspond to those elements previously described.

Figure 7E:
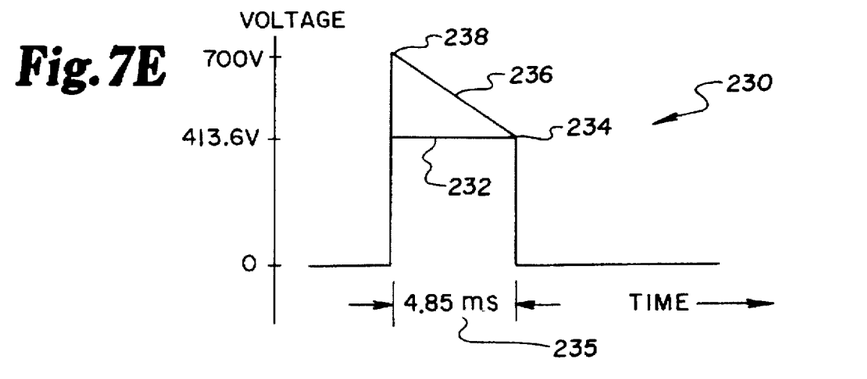
FIG. 7E illustrates the voltage-time waveform of a particular monophasic pulse achieved by using a current limiter, with the lower trace representing the rectangular voltage-time waveform delivered to the defibrillation path; and, FIG. 7F illustrates the current-voltage characteristic of a bilaterally symmetric current limiters, specifically a floating-gate JFET.

FIG. 7E illustrate a voltage-time waveform 230 of a particular monophasic pulse achieved by using a current limiter, with the lower trace 232 representing the rectangular voltage-time waveform delivered to the defibrillation path, having an amplitude 234 and a pulse duration 235, a and having an upper trace 236 with an initial amplitude 238 where all numerals correspond to those elements previously described.

Figure 7F:
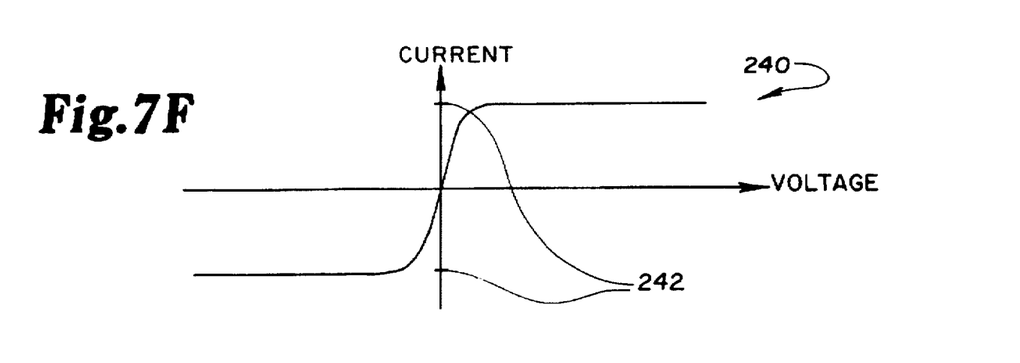

FIG. 7F illustrates the current-voltage characteristic 240 of a bilaterally symmetric current limiters, specifically a floating-gate JFET, having a characteristic-current magnitude 242 in either polarity where all numerals correspond to those elements previously described.

MODE OF OPERATION

The defibrillation electrodes whose implantation is least costly and risky to a patient are somewhat less efficient than those attached directly to the heart exterior. Examples in the former category are endocardial coils, positioned on the exterior of cardiac catheter that is introduced transvenously into the interior of the heart. Among these coil options is the right-ventricular-apex (RVA) electrode. Other positional options for an endocardial coil are inside the right atrium, or inside the coronary sinus, or inside the superior vena cava (SVC). These last three positions are comparatively close together in the heart, and are for convenience here lumped and labeled "SVC". The present invention improves the performance of these easier-to-implant electrodes by modifying the pattern of energy and current delivery that occurs naturally when two or more defibrillation-current pathways are created by means of these four or six electrode options. The natural pattern is determined by the respective path resistances.

Modifications of the pattern not only yields more efficient defibrillation., but also diminishes tissue damage resulting from excessive current in low-resistance paths. The modification is achieved in the invention by, for example, assigning to a lower-resistance path a (1) smaller pulse duration, or (2) a lower-voltage capacitor discharge. The second method comprises the options of capacitor switching, or of introducing a lossy element in series in such a path or paths. Particularly advantageous is the use of a current limiter as the lossy element, because it is capable of generating a pulse of rectangular waveform, a technique useful for both single-path and multiple-path situations. Such a pulse delivers a maximum of energy for a given peak-field value with a particular electrode combination and pulse duration. Peak field is a measure of the tissue-damage potentiality of a particular discharge.

Various modifications can be made to the present invention without departing from the apparent scope hereof.

We claim:

1. An implantable defibrillator system having multiple pathways for applying electrical countershocks to a heart of a human patient, the system comprising:
  a capacitor energy storage system;
  a power supply connected to the capacitor system;
  a detection system for detecting a cardiac dysthythmia in the patient;
  at least first, second and third implantable electrodes providing at least a pair of discharge pathways through which countershocks may be applied; and
  a controller operably connected to the detection system, the capacitor system, the power supply and the electrodes which, in response to the detection system, selectively charges and discharges the capacitor system to generate a countershock, the countershock being applied through a second discharge pathway at a predetermined time after the countershock has been applied to a first discharge pathway such that both the first and second discharge pathways are energized concurrently.

2. The system as in claim 1, wherein the energy to both the first and second discharge pathways is terminated simultaneously.

3. The system as in claim 1, wherein the first electrode is a plurality wire array electrode.

4. The system as in claim 1, wherein the second electrode is an active housing electrode.

5. The system as in claim 1, wherein the third electrode is a super vena cava coil electrode.

6. A method of applying countershocks to a plurality of pathways in an implantable defibrillator system wherein the implantable defibrillator system includes a capacitor energy storage system, a power supply for charging the capacitor system, a detection system, first, second and third electrodes forming at least a pair of discharge pathways, and a controller, the method comprising the steps of:
  supplying a discharge voltage to the capacitor energy storage system from the power supply;
  applying a discharge voltage from the capacitor to a first discharge pathway; and
  applying the discharge voltage from the capacitor to a second discharge pathway at a predetermined time after the discharge voltage is applied to the first discharge pathway such that both the first and second discharge pathways are energized concurrently.

7. The method as in claim 6 further including the step of simultaneously terminating the voltage to both the first and second discharge pathways.

8. An implantable defibrillator system that selectively applies countershocks to a plurality of electrodes to avoid tissue damage, the system comprising:
  a capacitor energy storage system;
  a power supply connected to the capacitor system, wherein the power supply charges the capacitor system;
  a first electrode having a first impedance and a second electrode having a second impedance wherein the first and second electrodes are connected to the capacitor energy storage system and implantable in a human body and wherein the impedance of the first electrode is less than the impedance of the second electrode; and
  a control device that controls the discharge of energy from the capacitor system to the first and second electrodes wherein energy is discharged to the second electrode a predetermined time after energy has been discharged to the first electrode and wherein the energy discharged from the capacitor decays over time such that the energy applied to the first electrode is greater than the energy applied to the second electrode such that tissue adjacent to the first electrode receives a peak voltage below a predetermined tissue damage threshold and such that tissue adjacent to the second electrode receives a peak voltage below the predetermined tissue damage threshold.

9. The system as in claim 8 further comprising a third electrode having a third impedance wherein the third electrode is connected to the capacitor energy storage system and wherein the impedance of the third electrode is greater than the impedance of the first and second electrodes.

10. The system as in claim 9, wherein energy is discharged to the third electrode a predetermined time after energy has been discharged to the second electrode such that tissue adjacent to third electrode receives a peak voltage below a predetermined tissue damage threshold.

* * * * *